US012708298B2

(12) United States Patent
Lee

(10) Patent No.: US 12,708,298 B2
(45) Date of Patent: Aug. 18, 2026

(54) CONTINUOUS ANALYTE METER HAVING SWITCH ACTIVATOR INTERWORKING WITH ACTUATOR

(71) Applicant: UXN Co., Ltd., Gyeonggi-do (KR)

(72) Inventor: Kyu Jin Lee, Seoul (KR)

(73) Assignee: UXN Co., Ltd., Gyeonggi-do (KR)

( * ) Notice: Subject to any disclaimer, the term of this patent is extended or adjusted under 35 U.S.C. 154(b) by 381 days.

(21) Appl. No.: 18/278,076

(22) PCT Filed: May 23, 2023

(86) PCT No.: PCT/KR2023/006989

§ 371 (c)(1),
(2) Date: Aug. 21, 2023

(87) PCT Pub. No.: WO2023/229337

PCT Pub. Date: Nov. 30, 2023

(65) Prior Publication Data

US 2025/0025075 A1 Jan. 23, 2025

(30) Foreign Application Priority Data

May 23, 2022 (KR) ........................ 10-2022-0063135
May 23, 2022 (KR) ........................ 10-2022-0063151

(51) Int. Cl.
*A61B 5/1473* (2006.01)
*A61B 5/00* (2006.01)

(52) U.S. Cl.
CPC .......... *A61B 5/1473* (2013.01); *A61B 5/6813* (2013.01); *A61B 2560/0209* (2013.01); *A61B 2560/0214* (2013.01); *A61B 2560/0443* (2013.01); *A61B 2560/0462* (2013.01); *A61B 2560/06* (2013.01)

(58) Field of Classification Search
CPC .......................... A61B 5/1473; A61B 5/14532
See application file for complete search history.

(56) References Cited

U.S. PATENT DOCUMENTS

2009/0076360 A1* 3/2009 Brister ................. A61B 5/1411 204/403.01
2010/0198034 A1* 8/2010 Thomas ............... A61B 5/7405 600/365
2022/0225899 A1* 7/2022 Peterson ............ A61B 5/14503

FOREIGN PATENT DOCUMENTS

KR 2024020099 A * 8/2022

* cited by examiner

*Primary Examiner* — Jacqueline Cheng
*Assistant Examiner* — Tho Q Tran
(74) *Attorney, Agent, or Firm* — The PL Law Group, PLLC

(57) ABSTRACT

A continuous analyte meter may include an electrochemical sensor invasively inserted into the skin, a transmitter including a main substrate to which a battery is connected and a housing in which the main substrate is accommodated, the housing being attached to the skin and the main substrate controlling a signal measured by the electrochemical sensor, a needle inserting the electrochemical sensor into the skin, and an inserter provided with an actuator that moves the transmitter and the needle from a first position to a second position so that the needle penetrates the skin or retracts the needle from the second position to a third position.

14 Claims, 14 Drawing Sheets

CONTINUOUS ANALYTE METER HAVING SWITCH ACTIVATOR INTERWORKING WITH ACTUATOR

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/KR2023/006989, filed May 23, 2023, which claims priority to the benefit of Korean Patent Application Nos. 10-2022-0063135 filed on May 23, 2022, and 10-2022-0063151 filed on May 23, 2022 in the Korean Intellectual Property Office, the entire contents of which are incorporated herein by reference.

BACKGROUND

1. Technical Field

The present disclosure relates to a continuous analyte meter having a switch and a switch activator to enable starting of power supply during use.

2. Background Art

A proximal portion of an electrochemical sensor may be located opposite to a distal portion of the electrochemical sensor at least partially inserted into the body. The proximal portion of the electrochemical sensor may be electrically connected to a main substrate of a transmitter, which includes an electric circuit required to measure glucose.

The transmitter may be provided with a needle for inserting the electrochemical sensor into the skin of the body. The needle penetrated into the skin may be removed again out of the skin while keeping only the electrochemical sensor inserted into the skin.

Power may be supplied to operate the electrochemical sensor and the main substrate. At this time, the timing of starting power supply is important in consideration of the lifespan of a battery mounted in the transmitter.

SUMMARY

The present disclosure is intended to propose a continuous analyte meter having a switch activator that allows power supply to a transmitter to be started in conjunction with the operation of an actuator.

A continuous analyte meter according to the present disclosure may include: an electrochemical sensor invasively inserted into the skin; a transmitter including a main substrate to which a battery is connected and a housing in which the main substrate is accommodated, the housing being attached to the skin and the main substrate controlling a signal measured by the electrochemical sensor; a needle inserting the electrochemical sensor into the skin; and an inserter provided with an actuator that moves the transmitter and the needle from a first position to a second position so that the needle penetrates the skin or retracts the needle from the second position to a third position.

Here, a switch turning on/off power supply of the battery to the main substrate or the electrochemical sensor may be provided in the transmitter, and a switch activator interworking with the actuator and turning on the switch to start power supply of the battery may be provided.

As described above, the present disclosure has a structure in which a moving part inside an inserter operates a switch activator. Thus, power supply to a transmitter is started in conjunction with an attaching operation of the transmitter or a retracting operation of a needle, so waste of a battery can be prevented and its lifespan can be extended.

BRIEF DESCRIPTION OF THE DRAWINGS

FIG. 1 is a perspective view illustrating a continuous analyte meter including an inserter, a transmitter, and an electrochemical sensor according to the present disclosure.

FIG. 3 is a plan view of FIG. 2.

FIG. 10 is a sectional view illustrating a state in which the inserter is separated from the skin while a switch of the transmitter is turned on.

DETAILED DESCRIPTION

Figure 2:
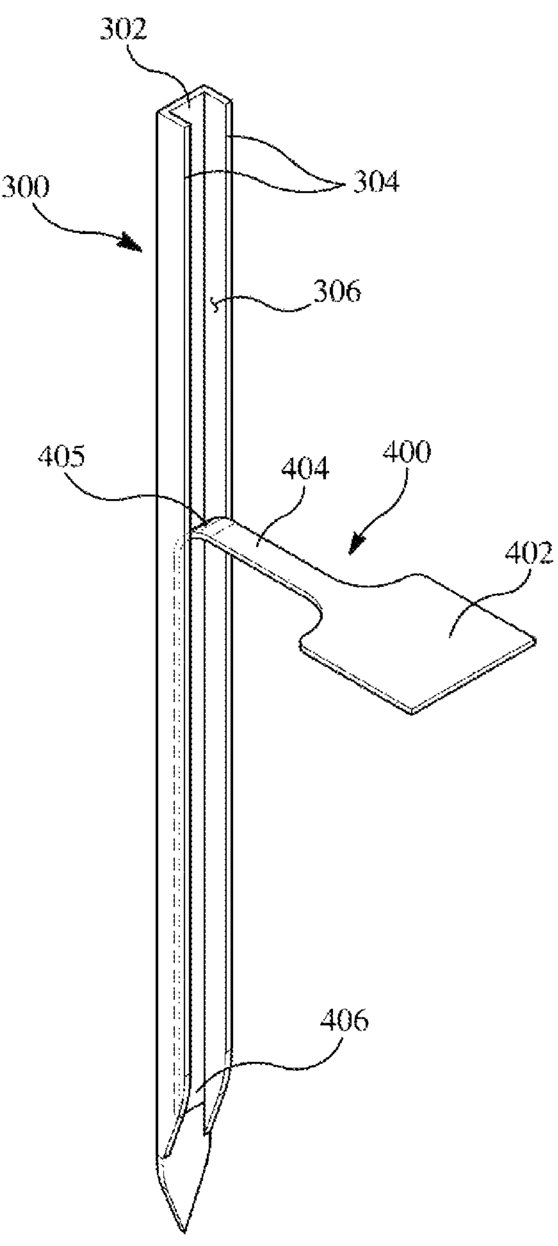
FIG. 2 is an assembled perspective view illustrating a needle and an electrochemical sensor according to an embodiment of the present disclosure.
Figure 4:
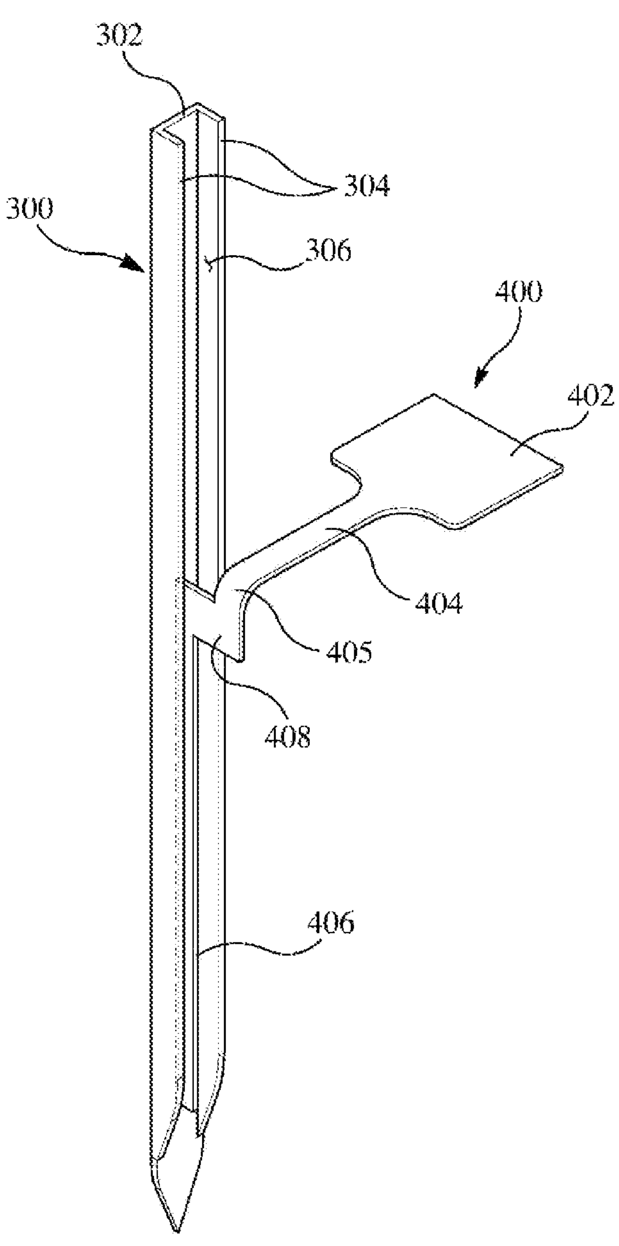
FIG. 4 is an assembled perspective view according to another embodiment of FIG. 2.
Figure 5:
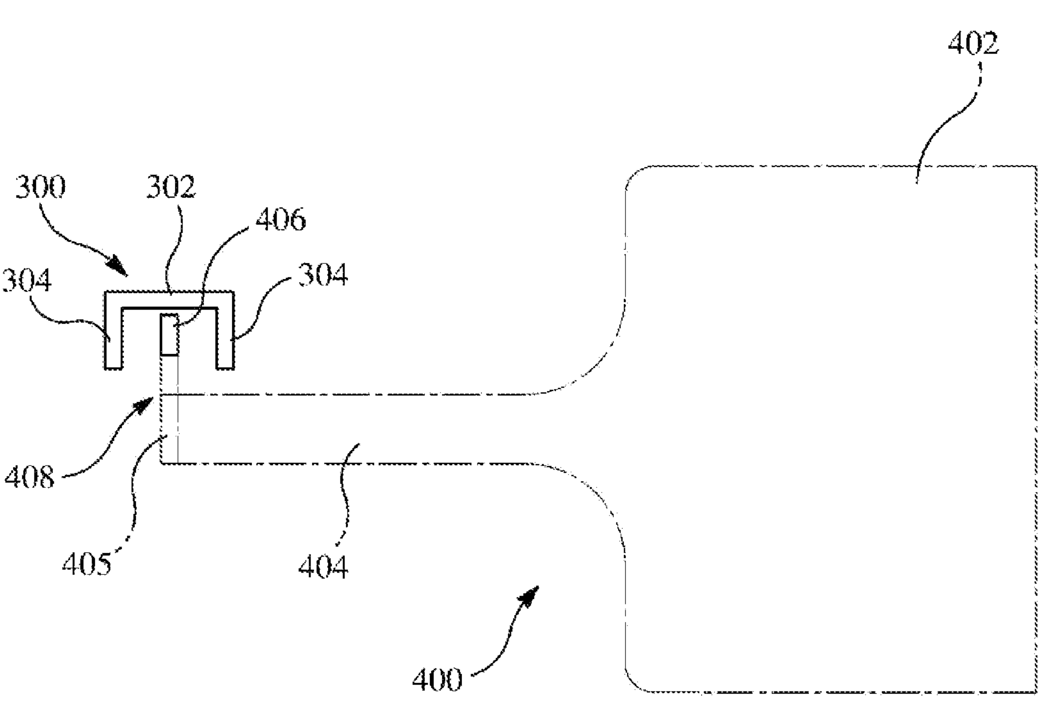
FIG. 5 is a plan view of FIG. 4.

Hereinafter, a case in which an electrochemical sensor 400 according to the present disclosure is used in a continuous glucose monitoring system (CGMS) for measuring the concentration of glucose in interstitial fluid or blood will be described as an example. However, a continuous analyte meter according to the present disclosure is not limited to measuring the concentration of glucose in the body and can be extensively applied to continuous analyte meters that measure other bio-markers.

<Inserter>

Figure 1:
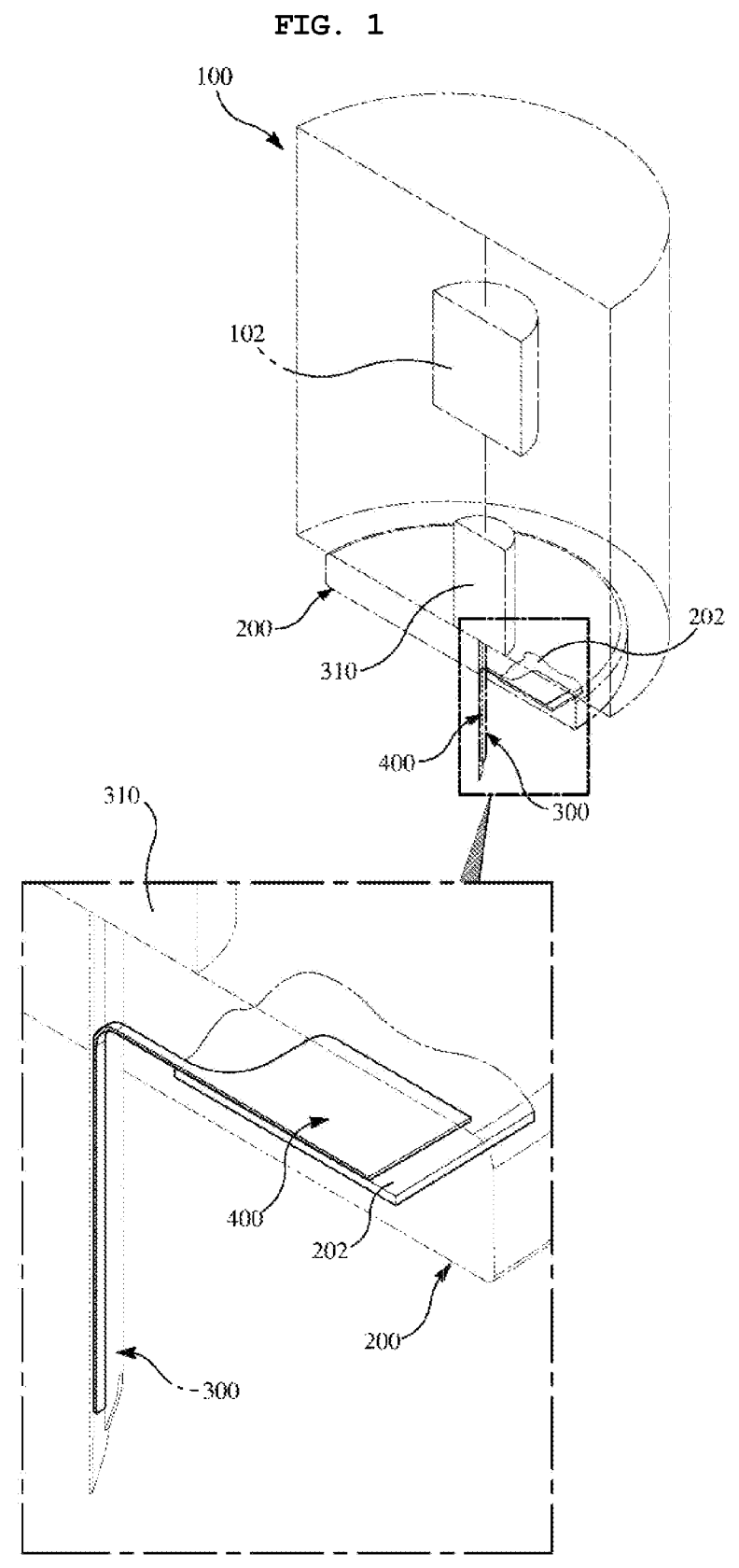

Referring to FIG. 1, the electrochemical sensor 400 according to the present disclosure may be attached to the skin along with a transmitter 200. The transmitter 200 may control a signal measured by the electrochemical sensor 400 and continuously transmit a measured blood glucose level to an external terminal including a mobile phone.

The external terminal may be provided separately from the transmitter 200 attached to the skin, and continuously receive measurement data of the electrochemical sensor 400 wirelessly from the transmitter 200. A user may continuously monitor and diagnose measurement data of the electrochemical sensor 400 for bio-markers including glucose, lactate, and the like.

The electrochemical sensor 400 and the transmitter 200 may be provided to the user in a state of being loaded in an inserter 100 before being attaching to the skin. By a user's attachment motion, the electrochemical sensor 400 and the transmitter 200 may be detached from the inserter 100 and attached to the skin.

A first end of the electrochemical sensor 400 connected to an electrical part of the transmitter 200 including a main substrate 202 may be referred to as a proximal portion 402, a second end of the electrochemical sensor 400 at least partially invasively inserted into the body may be referred to as a distal portion 406, and a portion that interconnects the proximal portion 402 and the distal portion 406, is disposed between the proximal portion 402 and the distal portion 406, and is flexibly bendable may be referred to as a bending portion 405.

Invasive insertion as used herein may refer to inserting at least a portion of the distal portion 406 of the electrochemical sensor 400 into the body.

The transmitter 200 and the electrochemical sensor 400 may be provided to the user in a state in which they are already connected to each other prior to being attached to the skin.

The transmitter 200 may be located in a first position in a state of being loaded in the inserter 100. The transmitter 200 may be moved from the first position to a second position by a user's motion. The transmitter 200 may be attached to the skin in the second position. An insertion direction of the transmitter 200 and the electrochemical sensor 400 may refer to a direction from the first position to the second position.

A needle 300 may have an exposed portion exposed in the longitudinal direction thereof. A portion of the electrochemical sensor 400 may be disposed inside the needle 300. The needle 300 may serve to incise the skin and guide the electrochemical sensor 400 so that at least a portion of the distal portion 406 is invasively inserted into the body along the insertion direction.

The inserter 100 may include an actuator 102 that operates the transmitter 200 and the electrochemical sensor 400 from the first position to the second position or returns the needle 300 from the second position to a third position.

The actuator 102 may advance the needle 300 or the transmitter 200 from the first position to the second position so that the needle 300 or the distal portion 406 is inserted into the skin.

After the transmitter 200 and the electrochemical sensor 400 are attached to the skin in the second position, the actuator 102 may retract the needle 300 from the second position to the third position so that the needle 300 is separated from the transmitter 200 and the electrochemical sensor 400.

The actuator 102 may be connected to a needle handle 310 to which the needle 300 is fixed. The needle handle 310 may be detachable from the actuator 102. The actuator 102 may include a return member 103 to which the needle handle 310 is detachably coupled.

An inner space may be provided between an upper cover and a 5 lower cover of the transmitter 200. The main substrate 202 may be seated in the inner space of the transmitter 200.

The main substrate 202 may be provided with at least one of a power supply unit such as a battery required to measure the glucose concentration by the distal portion 406, a control unit including an electric circuit, a wireless communication unit for controlling data measured by the electrochemical sensor 400 and wirelessly transmitting the data to the outside, and an operational amplifier.

The power supply unit may supply a bias voltage that can generate an electrochemical reaction of a working electrode.

A signal of an analyte measured at the distal portion 406 may be amplified by the operational amplifier.

The magnitude of an output current for a given bias on the working electrode may be a measure of the concentration of the analyte, such as glucose, in the vicinity of an electrode 424.

The control unit including the electrical circuit may control the electrical potential between the working electrode and a reference electrode at one or more preset values.

A first surface of the electrochemical sensor 400 on which a sensor pad 428 is formed may face the main substrate 202, and a second surface of the electrochemical sensor 400 may be exposed to the inner space of the transmitter 200.

The sensor pad 428 may be formed at the proximal portion 402 of the electrochemical sensor 400. A contact pad electrically connected to the sensor pad 428 may be formed on the main substrate 202.

Since at least a portion of the electrochemical sensor 400 is invasively inserted into the skin, the electrochemical sensor 400 or a base layer 410 may be flexible to relieve pain during invasive insertion and reduce discomfort during wearing.

The distal portion 406 of the electrochemical sensor 400 may be disposed at the exposed portion of the needle 300 exposed along the longitudinal direction thereof. An end of the needle 300 may be in a more protruding position than an end of the distal portion 406. The distal portion 406 of the electrochemical sensor 400 may be inserted into the body after the skin is incised by the needle 300.

Pain relief and discomfort reduction are key performances of the continuous analyte meter from the user's point of view. To this end, the electrochemical sensor 400 has flexibility that it is impossible to penetrate the skin alone, and the electrochemical sensor 400 is thin and flexible enough to be inserted into the body only after the needle 300 incises the skin.

<Needle and Electrochemical Sensor>

The arrangement relationship between the needle 300 and the electrochemical sensor 400 will be described with reference to FIGS. 2 to 5.

The needle 300 may have an open portion 306 exposing the inside of the needle 300 to the outside and extending along the longitudinal direction of the needle 300. A portion of the distal portion 406 or the bending portion 405 may be attached to or face the needle 300 so as to be located inside the open portion 306 upon invasive insertion into the body.

The distal portion 406 and the proximal portion 402 may lie on different planes having a predetermined angle. A bending direction of the bending portion 405 may coincide with a direction in which the inside of the needle 300 is exposed to the outside by the open portion 306.

A portion where the proximal portion 402 is electrically connected to the transmitter 200 may be located in a direction in which the inside of the needle 300 is exposed to the outside by the open portion 306.

For example, the distal portion 406 may be inserted orthogonal to the skin surface to reduce pain and discomfort. When the main substrate 202 is positioned parallel to a bottom surface of the transmitter 200, the proximal portion 402 may be positioned parallel to the main substrate 202, and the proximal portion 402 may be positioned parallel to the skin surface. In this case, the proximal portion 402 parallel to the skin and the distal portion 406 orthogonal to the skin may lie on different planes orthogonal to each other. The bending portion 405 may be bent along a direction in which the inside of the needle 300 is exposed to the outside.

The needle 300 may include a central wall portion 302 guiding invasive insertion of the electrochemical sensor 400, and opposite portions sidewall 304 preventing the electrochemical sensor 400 from being separated from the needle 300 during invasive insertion.

The central wall portion 302 may prevent the distal portion 406 or the bending portion 405 from protruding in a first axial direction. The first axial direction may refer to a direction in which the inside of the needle 300 is exposed to the outside. When the distal portion 406 or the bending portion 405 protrudes in the first axial direction, the electrochemical sensor 400 may be buckled as a protruding portion thereof is caught on the skin, and only the needle is inserted into the skin but the electrochemical sensor 400 may be come out of the skin.

The sidewall portions 304 may prevent a portion of the distal portion 406 or the bending portion 405 from being displaced in a second axial direction. The second axial direction may refer to a direction orthogonal to the first axial direction. The first axial direction, the second axial direction, and the insertion direction may correspond to the axes of an orthogonal coordinate system.

The sidewall portions 304 may be disposed to have a predetermined angle with the center wall portion 302. The predetermined angle may be an angle within a range of 0 to 180 degrees with respect to surfaces of the sidewall portions 304 facing the electrochemical sensor 400.

The inner space of the needle 300 surrounded by the central wall portion 302 and the sidewall portions 304 may communicate with the outside through the open portion 306.

The electrochemical sensor 400 may have a flat plate shape. The electrode 424 of the distal portion 406 may be disposed on one or opposite surfaces of a flat plate portion.

Figure 3:
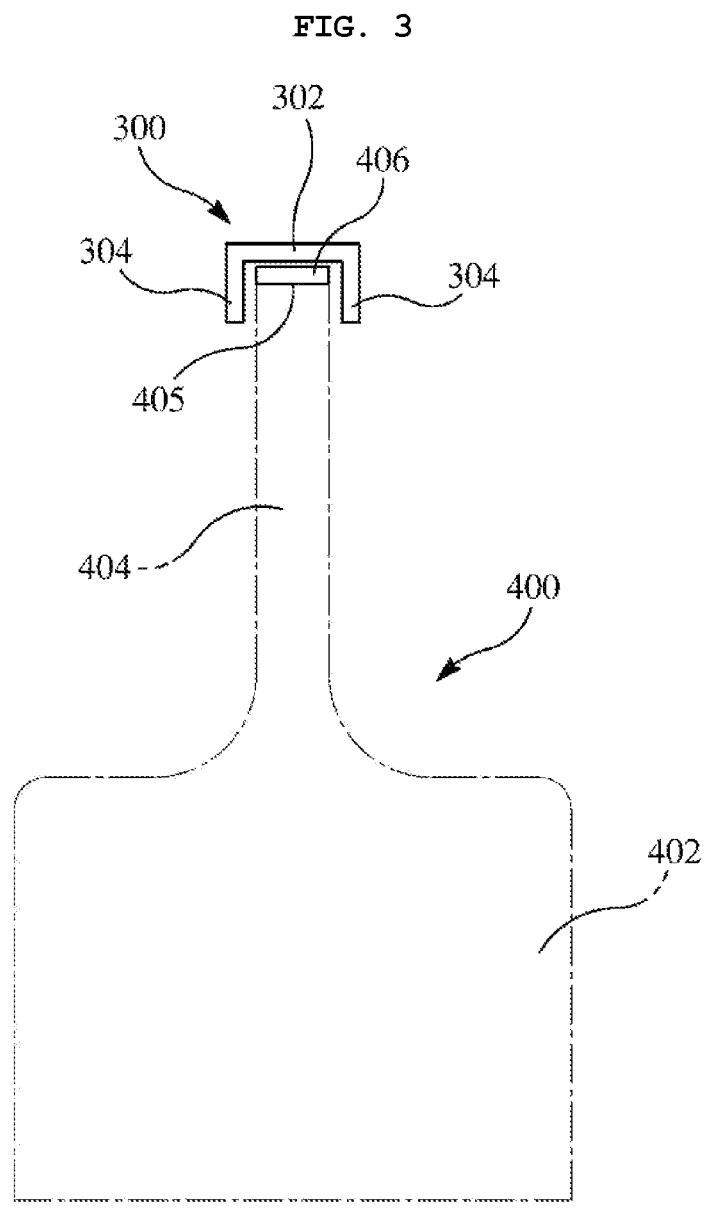

The first embodiment illustrated in FIGS. 2 and 3 may be a case in which the central wall portion 302 faces the electrochemical sensor 400 in parallel. The second embodiment illustrated in FIGS. 4 and 5 may be a case in which the central wall portion 302 faces the electrochemical sensor 400 orthogonally.

In the case of the first embodiment, the electrode 424 may make large-area contact with the outside through the open portion 306. The bending portion 405 may be bent without twisting or changing direction. In the case of the first embodiment, the bending portion 405 may be bent only one time. In this case, a torsional load applied to the bending portion 405 may be low, thereby reducing stress required to maintain a bent state.

In the case of the second embodiment, the electrochemical sensor 400 may be bent while twisting or changing in direction. The intermediate portion 404 may be bent while twisting a plurality of times or changing in direction a plurality of times so that the intermediate portion 404 extends to the proximal portion 402 while avoiding the sidewall portions 304 of the needle 300.

A side extension portion 408 may be formed so that the number of twists of the intermediate portion 404 twisting until reaching the main substrate 202 is reduced and the sidewall portions 304 of the needle 300 being raised is not caught by the intermediate portion 404 or the proximal portion 402 of the electrochemical sensor 400.

The side extension portion 408 may be a portion extending from the intermediate portion 404 in the first axial direction between the distal portion 406 and the proximal portion 402. The intermediate portion 404 adjacent to the distal portion 406 may lie on the same plane as the distal portion 406. Thus, the side extension portion 408 may be a portion extending from the intermediate portion 404 on the same plane as the distal portion 406 in the first axial direction in which the inside of the needle 300 is exposed to the outside.

In the case of the second embodiment, notches may be formed by partially cutting the intermediate portion 404 at positions adjacent to the bending portion 405. This is to minimize twisting or bending of a portion of the intermediate portion 404 with respect to the bending portion 405.

Figure 6:
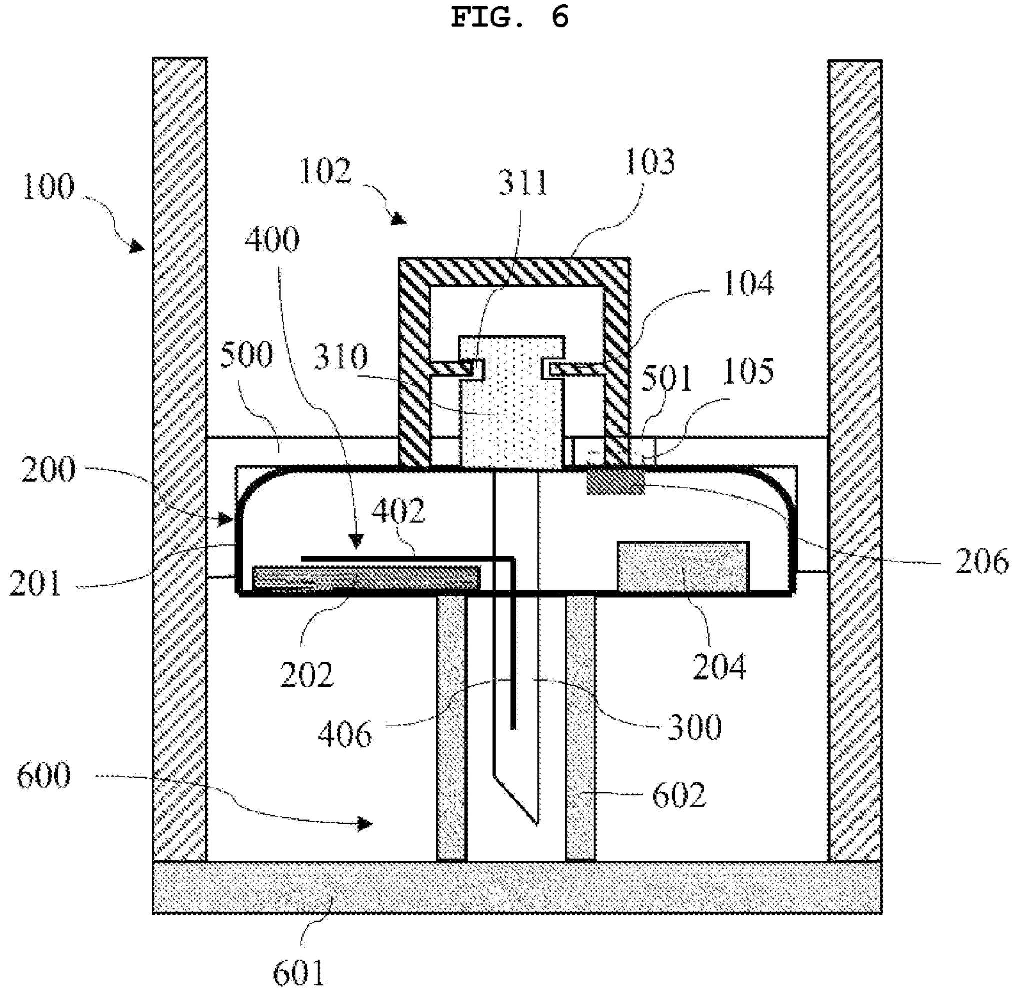
FIG. 6 is a schematic assembled sectional view illustrating the continuous analyte meter according to the present disclosure.

Referring to FIG. 6, the actuator 102 provided inside the inserter 100 may include the return member 103 moved together with the needle 300 and the needle handle 310.

The return member 103 may include a locking protrusion 104 detachably coupling the needle handle 310 to the return member 103.

The locking protrusion 104 may have elasticity and may be caught in a locking groove 311 of the needle handle 310. Therefore, the needle handle 310 may be separated from the inside of the return member 103 by applying a pulling force to the needle handle 310 when necessary.

The transmitter 200 may include a housing 201 having an inner space and facing the skin of the body. The housing 201 may include therein the main substrate 202, and a battery 204 for power supply.

The housing 201 of the transmitter 200 may be provided with a toggle switch 206 for turning on/off power supply of the battery 204. When the switch 206 is pressed, power supply from the battery 204 to the main substrate 202 may be blocked, and when pressing of the switch 206 is released, power supply may be started.

A transmitter support 500 detachably coupled to the transmitter 200 may be provided. The transmitter support 500 may suspendedly support the transmitter 200.

A switch activator that turns on the switch to start power supply of the battery may interwork with the actuator. That is, the switch activator may be installed on an operating part of the actuator.

When contact between the switch activator and the switch is released, the switch may be turned on.

An initial position may be a first time point. At the first time point, the switch may be always in an off state.

When the switch activator and the switch are in contact with each other and interfere with each other, the switch may be turned off. When the transmitter is in the first position, the switch may be turned off by contact interference between the switch activator and the switch.

As an embodiment, the switch may be turned on after the first time point.

A time point at which contact between the switch activator and the switch is released may be when the transmitter is moved out of the first position after the first time point at which the transmitter is in the first position. For example, when the switch activator is installed on the return member, the time point at which the switch activator is separated from the switch is when the needle is retracted and the transmitter is moved out of the first position.

As another embodiment, the switch may be turned on after the transmitter is attached to the skin.

The second position may be a position where the transmitter and the needle are moved together, the transmitter is attached to the skin, and the needle is inserted into the skin. A time point at which the transmitter and needle are in the second position may be a second time point.

A time point at which the needle is moved toward the third position after the second time point may be a third time point. A time point at which contact between the switch activator and the switch is released may be the third time point. The switch activator may be disposed on the return member. When the return member is moved toward the third position, contact of the switch activator with the switch may be released and the switch may be turned on.

The transmitter support and the return member may be moved together by the actuator from the first position to the second position.

The return member may be separated from the transmitter support and only the return member may be moved by the actuator from the second position to the third position. When the return member is separated from the transmitter support, contact of the switch activator with the switch may be released and the switch may be turned on.

When the transmitter is in the first position and the second position, the switch activator and the switch may be in contact with each other and interfere with each other and the switch may be kept in an off state.

The transmitter support and the return member may be moved together by the actuator from the first position to the second position. Before the return member and the transmitter support are separated, the switch activator and the switch may be in contact with each other and interfere with each other and the switch may be kept in an off state.

Meanwhile, a protective cap 600 may be detachably coupled to an end of the inserter 100. The operation of the actuator 102 may be suppressed before the protective cap 600 is separated from the end of the inserter 100.

The protective cap 600 may be detachably coupled to the end of the inserter 100 by screwing or force fitting. When the protective cap is separated from the end of the inserter, the end of the inserter may be exposed. When the end of the inserter is placed on the skin and the operation of the actuator is started, the switch may be turned on in conjunction with the operation of the actuator.

The protective cap 600 may include a blocking member 601 coupled to the inserter 100 and a support member 602 protruding from one surface of the blocking member 601. The support member 602 may support one surface of the housing 201 of the transmitter 200 provided inside the inserter 100 so that the transmitter 200 is kept in a stationary state.

When using the analyte meter according to the present disclosure, first, as illustrated in FIG. 6, the sealed protective cap 600 may be separated from the end of the inserter 100. Since the protective cap 600 is detachably coupled to the end of the inserter 100, the protective cap 600 may be separated from the end of the inserter 100. When the protective cap 600 is separated, the state in which the movement of the transmitter 200 inside the inserter 100 is blocked by the support member 602 of the protective cap 600 may be released, so the transmitter 200 may be transitioned into a state in which it is movable inside the inserter 100.

Figure 7:
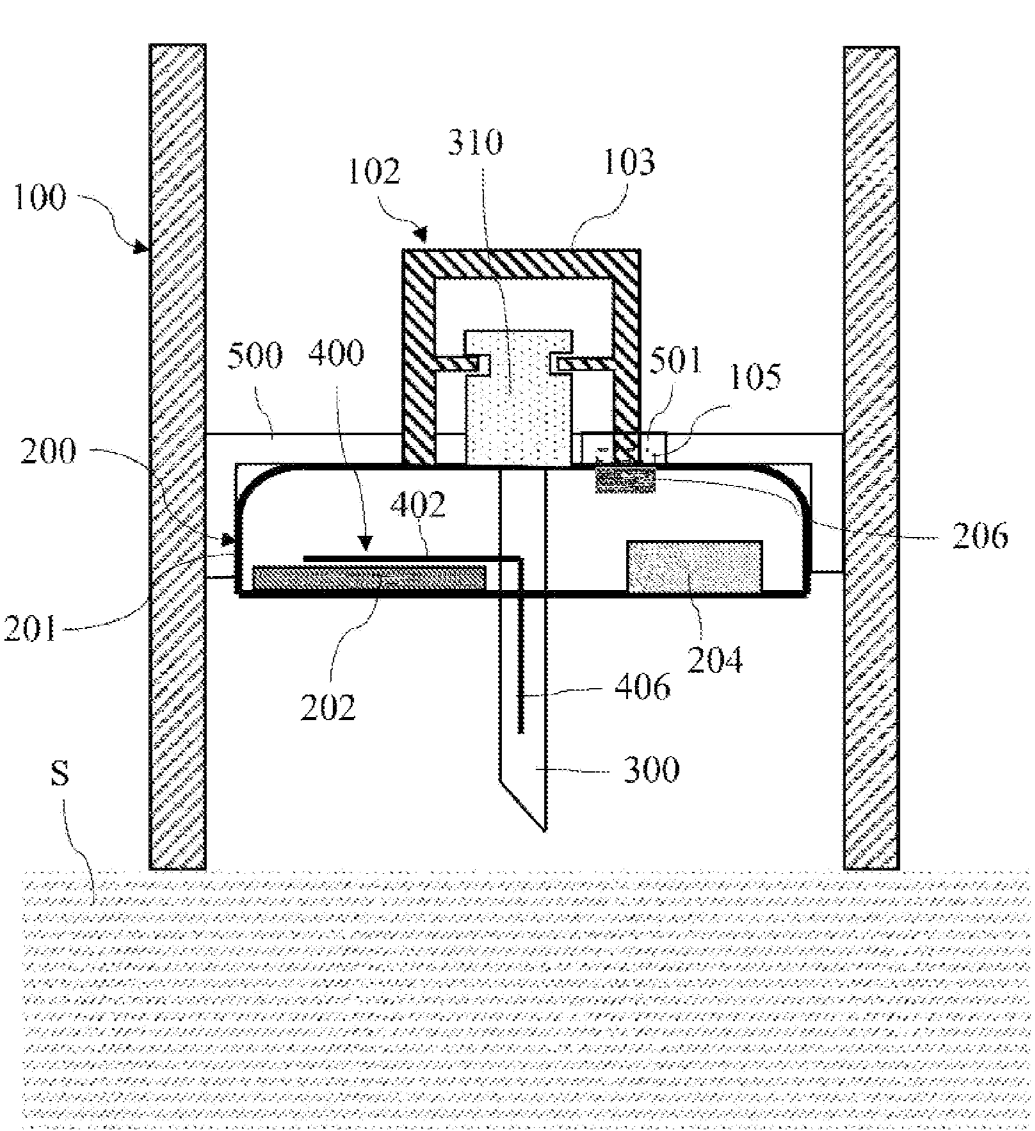
FIG. 7 is a sectional view illustrating a state in which a protective cap is removed and the inserter is in contact with the skin in the state of FIG. 6.
Figure 8:
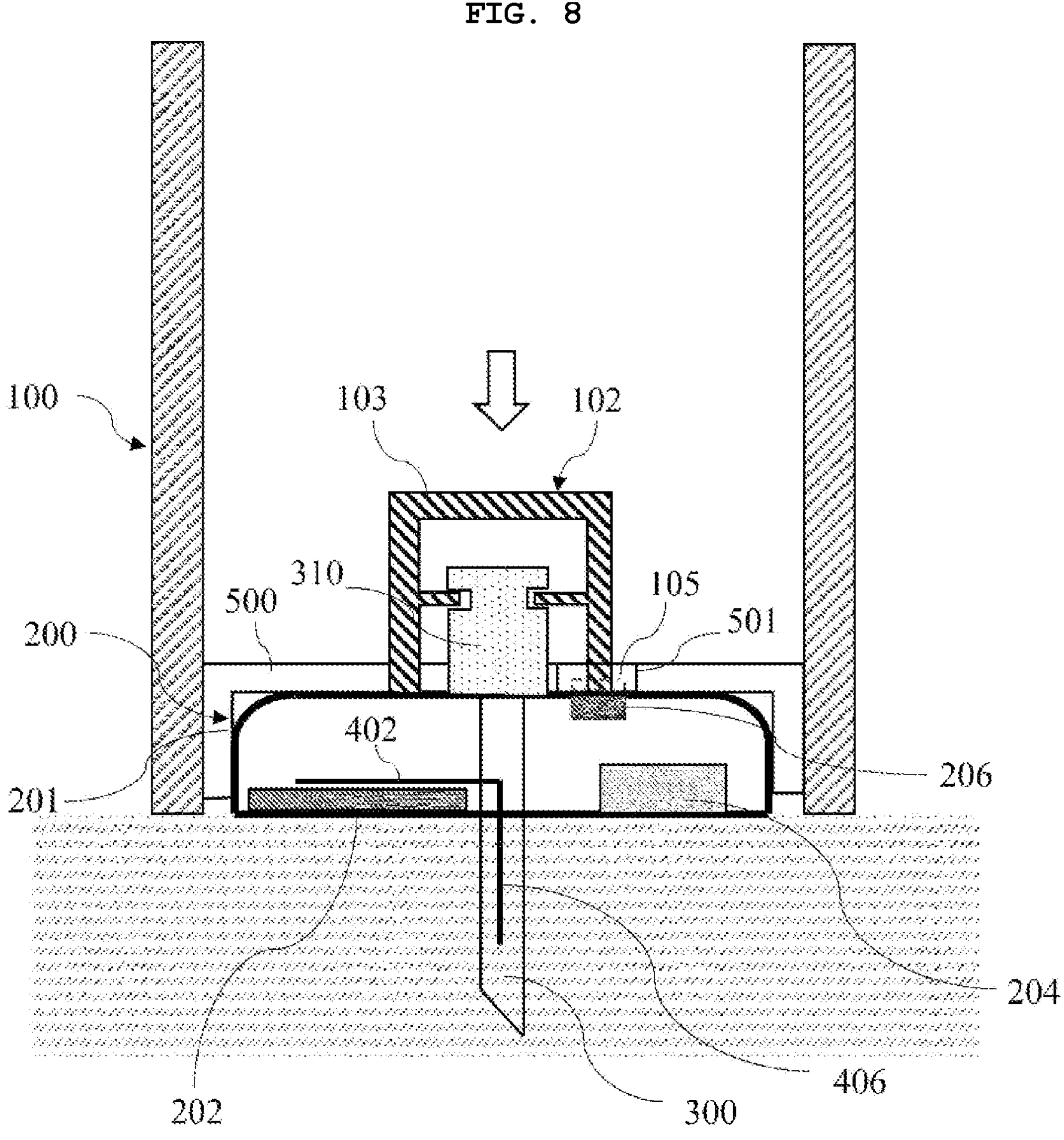
FIG. 8 is a sectional view illustrating a state in which the needle is inserted into the skin by moving an operating part inside the inserter while the inserter is in contact with the skin.

Referring to FIGS. 7 and 8, when the inserter 100 is brought into contact with the skin of the body and the actuator 102 is moved inside the inserter 100 to measure an analyte, the return member 103 corresponding to the actuator 102 may be moved from the first position to the second position, with the result that the transmitter support 500 coupled with the return member 103 may be moved toward the skin S at the same time. Since the transmitter support 500 is coupled to the housing 201 of the transmitter 200, the transmitter 200 may be moved simultaneously with the movement of the transmitter support 500.

The transmitter 200 provided with the electrochemical sensor 400 inside the inserter 100, the return member 103 coupled with the needle 300 and the needle handle 310, and the transmitter support 500 coupled with the transmitter 200 may be simultaneously moved from the first position before insertion into the skin to the second position where the needle 300 and the distal portion 406 of the electrochemical sensor 400 are inserted into the skin.

In addition, the needle handle 310 may be detachably coupled to the return member 103. When the return member 103 is returned, the needle 300 may be returned to the third position.

Figure 9:
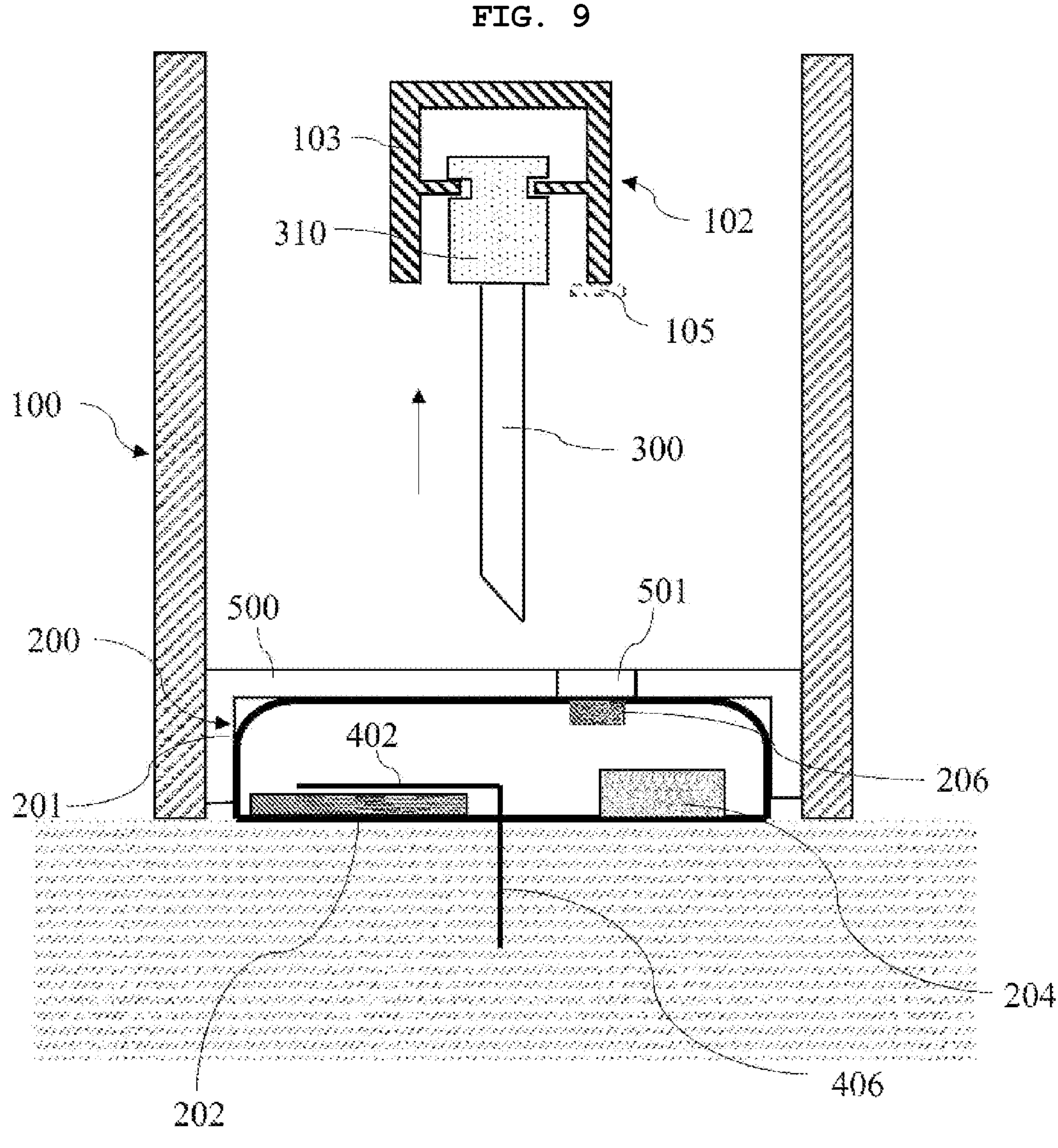
FIG. 9 is a sectional view illustrating a state in which power supply to the transmitter is started while the needle is removed out of the skin and separated from the transmitter by the movement of a return member in the state of FIG. 8.
Figure 10:
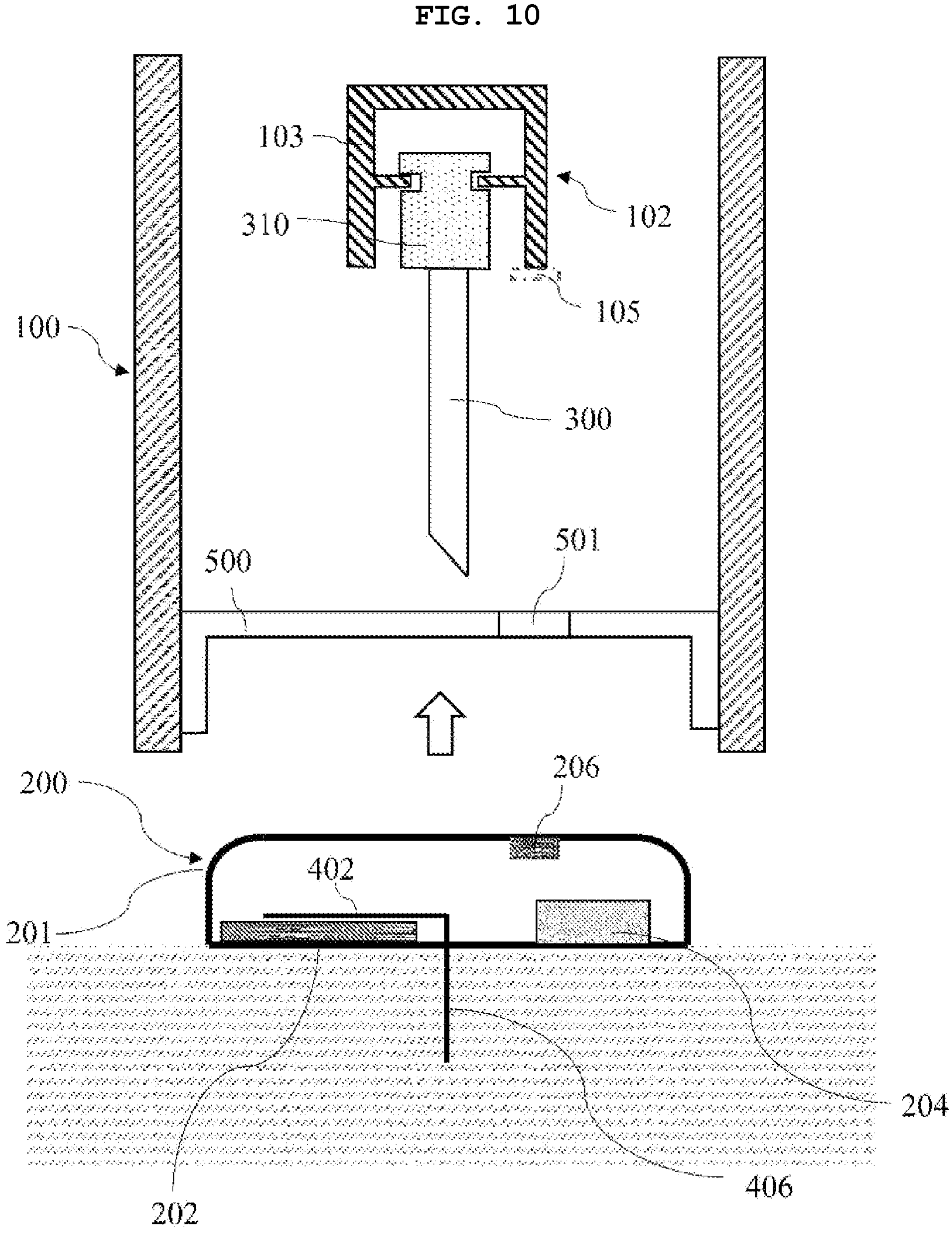

Referring to FIG. 9, since the needle handle 310 is coupled to the return member 103, the needle handle 310 may be moved away from the transmitter 200 and the transmitter support 500 by the return member 103, with the result that the needle 300 coupled to the needle handle 310 may be raised to the third position.

When the needle 300 is removed out of the skin by the movement of the return member 103 and then the inserter 100 is separated away from the skin, the transmitter support 500 provided in the inserter 100 may be moved together with the inserter 100 while being separated from the housing 201 of the transmitter 200. By the movement of the transmitter support 500, the coupled state with the transmitter 200 may be released.

When the device according to the present disclosure is not in use, the switch 206 may be in a state of being pressed by the switch activator 105 and thus may be kept in an off state.

When the pressed state by the switch activator 105 is released, the switch 206 may be activated and turned on. As power of the battery 240 is supplied thereby, sensing and control of a sensing operation by the main substrate 202 and the electrochemical sensor 400 may be activated, and an operation that allows the user to communicate and receive measurement information measured by the electrochemical sensor 400 in the skin may be activated.

<Another Embodiment of Switch Activator: Operation with Magnetic Force/Elastic Force>

The switch activator illustrated in FIGS. 1 to 10 is denoted by reference numeral 105.

Referring to FIGS. 11 to 14, another embodiment of a switch activator is illustrated. The switch activator operated by magnetic force/elastic force illustrated in FIGS. 11 to 14 is denoted by reference numeral 502.

A switch may include a power terminal 1206 and a moving magnet 207 movable while being spaced apart from the power terminal 1206. In addition, a conductive layer 208 coated with a conductive material may be formed on the moving magnet 207 of the switch, and a yoke member 209 made of a metal material may be provided on the power terminal 1206.

The yoke member 209 may be made of a metal material having magnetism, and may have a property of being attached to a magnet by attractive force when the magnet approaches the yoke member.

Thus, inside a housing 201 of a transmitter 200, the yoke member 209 may be in a stationary state, and the moving magnet 207 may be disposed in a movable state.

In addition, a transmitter support 500 detachably coupled to the transmitter 200 may be provided outside the transmitter 200. A switch activator 502 for performing a switching operation upon contact with the power terminal 1206 provided at one side of the housing 201 of the transmitter 200 may be provided at one side of the transmitter support 500.

The switch activator 502 provided at one side of the transmitter support 500 may be provided as a magnet having a magnetic force.

In another embodiment of a switch, a power terminal 1206 for turning on/off power supply of the battery 204 and a moving magnet 207 moving close to or away from the power terminal 1206 may be provided inside the housing 201. A conductive layer 208 coated with a conductive material for conducting electricity may be applied to at least one surface of the moving magnet 207.

An expanding and contracting member 207*a* may be formed on the moving magnet 207, and an elastic member 210 may be supported on an outer circumferential surface of the expanding and contracting member 207*a*. The elastic member 210 may be provided as, for example, a spring or the like.

Therefore, in a state in which the transmitter support 500 is coupled to the transmitter 200, the switch activator 502 may be close to the transmitter 200. Due to an attractive force between the moving magnet 207 and the switch activator 502, the moving magnet 207 may be moved toward the switch activator 502 while the expanding and contracting member 207*a* is contracted to compress the elastic member 210, with the result that the moving magnet 207 may be moved away from the power terminal 1206.

On the other hand, when the transmitter support 500 is separated and spaced apart from the transmitter 200, the switch activator 502 may be moved away from the transmitter 200. As the attractive force between the moving magnet 207 and the switch activator 502 is weakened or lost, the moving magnet 207 provided inside the transmitter 200 may face the power terminal 1206 by an elastic repulsive force of the elastic member 210 that has been compressed. Thus, the power terminal 1206 may be switched from an off state to an on state by the conductive layer 208 formed on the moving magnet 207.

In another embodiment, a switch activator 502 having a magnetic force may be provided on a transmitter support 500. Here, a guide protrusion 502*a* protruding out of the transmitter support 500 formed on the switch activator 502, and a through-hole 201*a* may be formed in a housing 201 of a transmitter 200. The guide protrusion 502*a* may be inserted into or separated from the through-hole 201*a*.

A through-hole may also be formed in a main substrate 202 provided inside the housing 201 of the transmitter 200 to communicate with the through-hole 201*a* formed in the housing 201.

In addition, a power terminal 1206 may be provided at one side of the main substrate 202, and a moving magnet 207 moving close to or away from the power terminal 1206 may be provided.

A conductive layer 208 coated with a conductive material for conducting electricity may be applied to at least one surface of the moving magnet 207. An elastic member 210 may be disposed on the moving magnet 207 so that an elastic repulsive force acts toward the power terminal 1206.

Thus, in a state in which the transmitter support 500 is coupled to the housing 201 of the transmitter 200, the moving magnet 207 provided inside the transmitter 200 may be pushed apart from the switch activator 502 by the magnetic force (repulsive force) between the moving magnet 207 and the switch activator 502 that have the same polarities. As a result, the moving magnet 207 may be disposed away from the power terminal 1206 while the elastic member 210 is compressed.

On the other hand, when the transmitter support 500 is separated and spaced apart from the housing 201 of the transmitter 200, as the magnetic force of the switch activator 502 is weakened or lost and the repulsive force between the switch activator 502 and the moving magnet 207 provided inside the transmitter 200 does not act. As a result, the moving magnet 207 may be moved by the elastic repulsive force of the elastic member 210 and face the power terminal 1206. Since the conductive layer 208 is applied to the moving magnet 207, when the moving magnet 207 faces the power terminal 1206, the power terminal 1206 may be switched from an off state to an on state, and thus power supply may be started.

Figure 11:
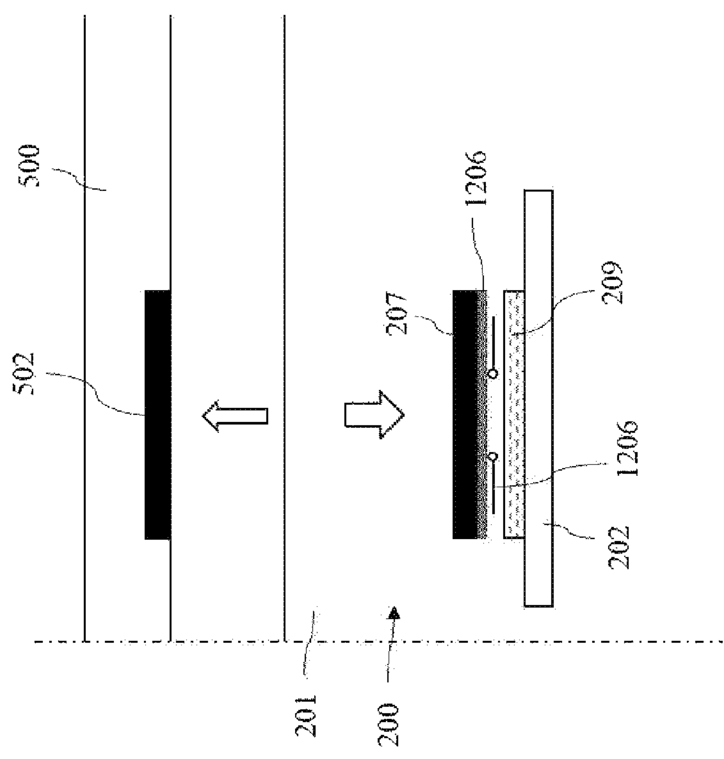
FIGS. 11 to 14 are views illustrating another embodiment of a switch activator, which operates by magnetic force/elastic force.
Figure 11:
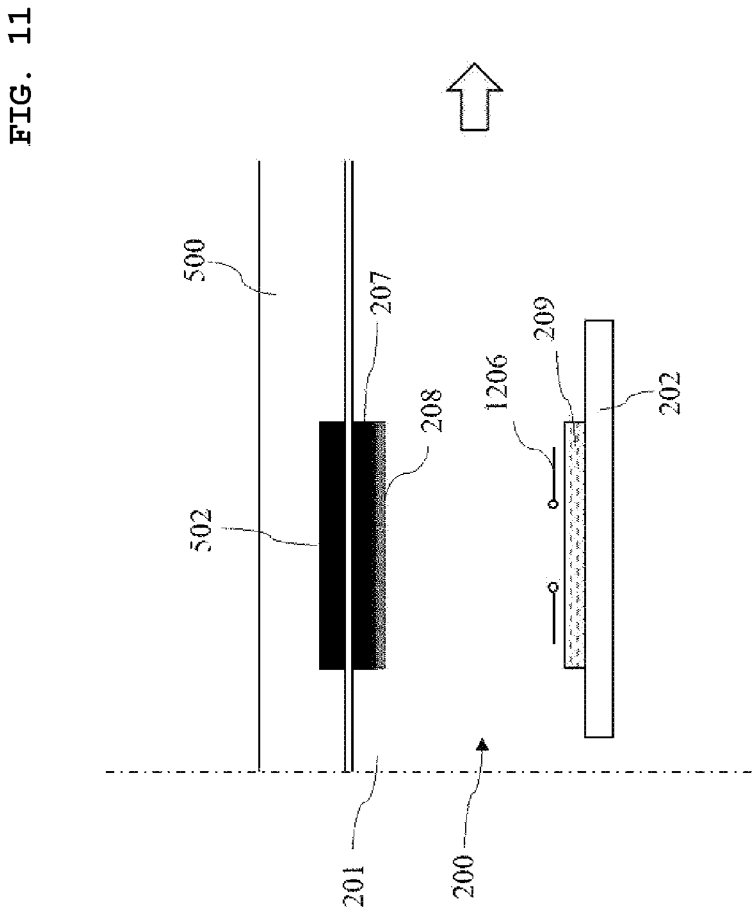
Figure 12:
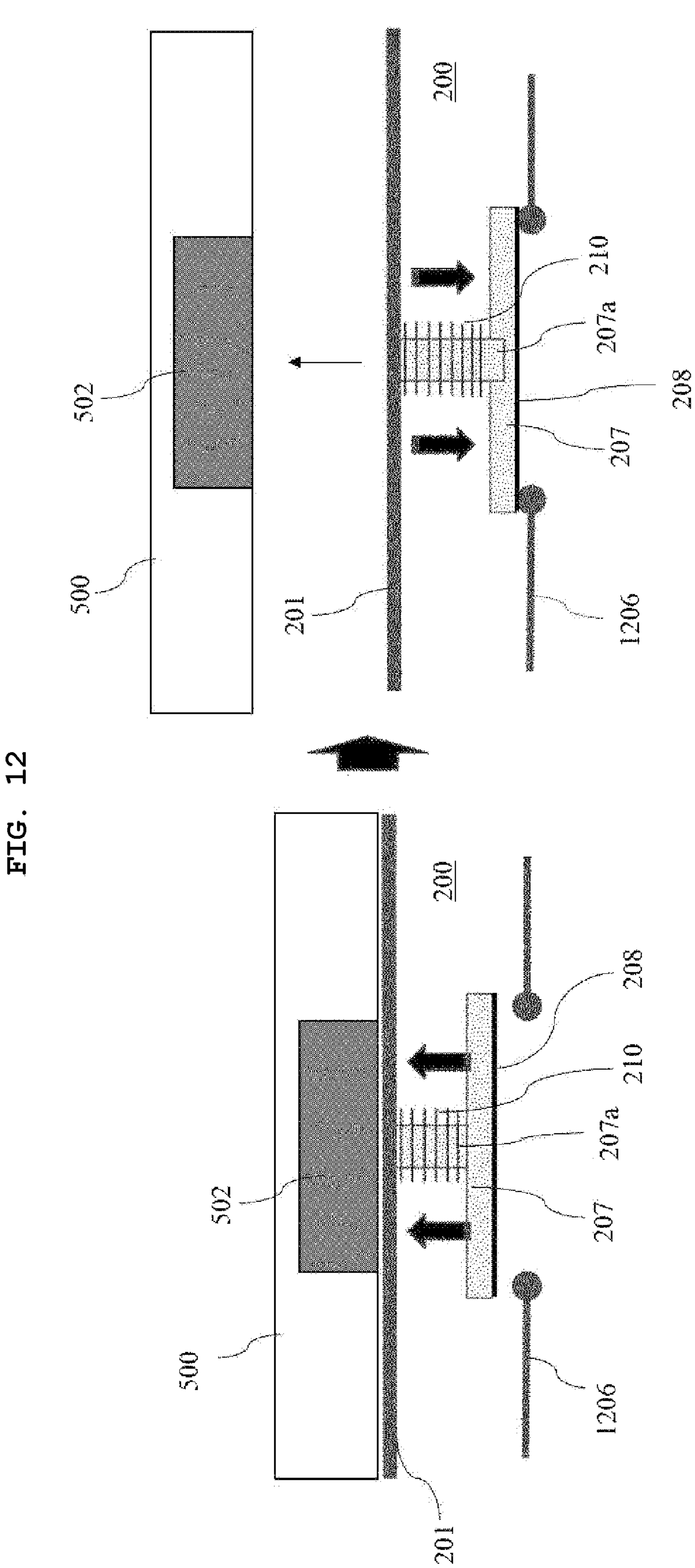
Figure 13:
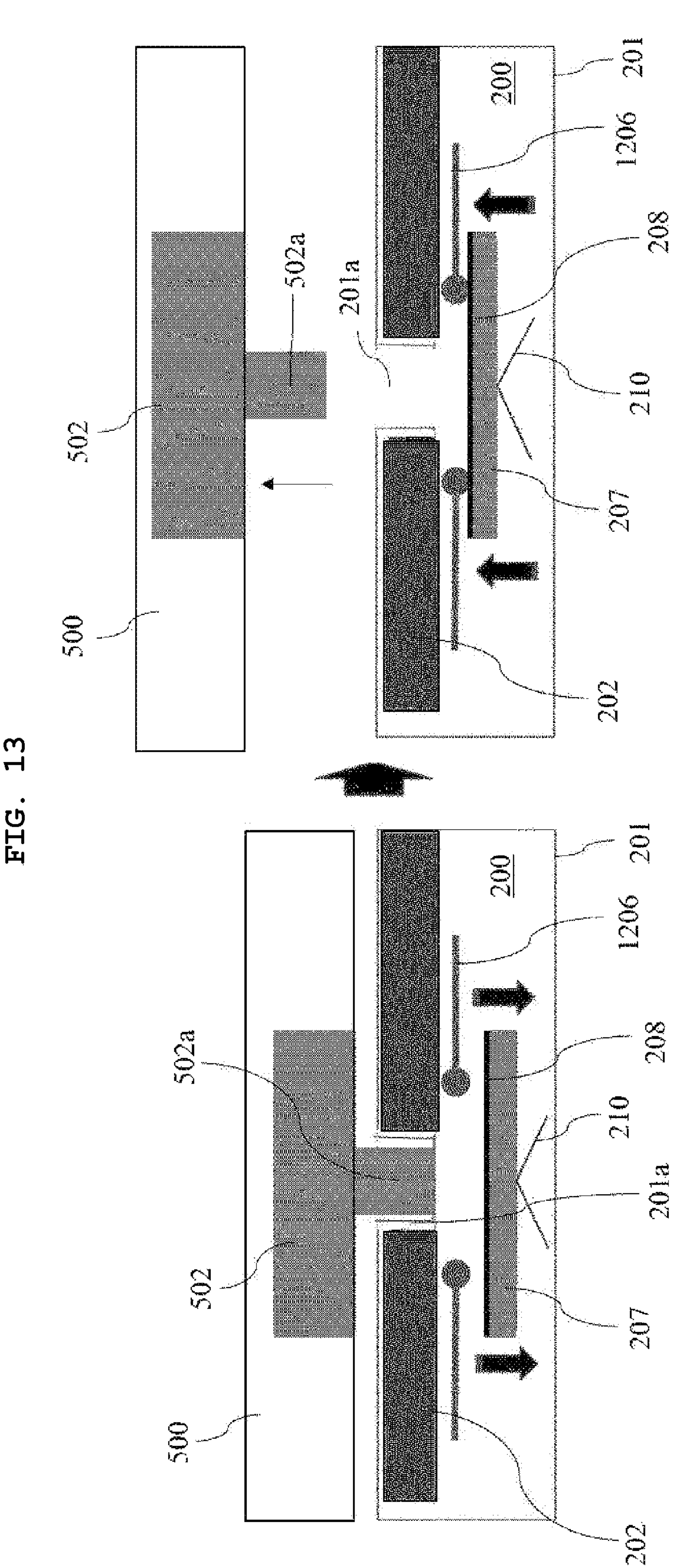
Figure 14:
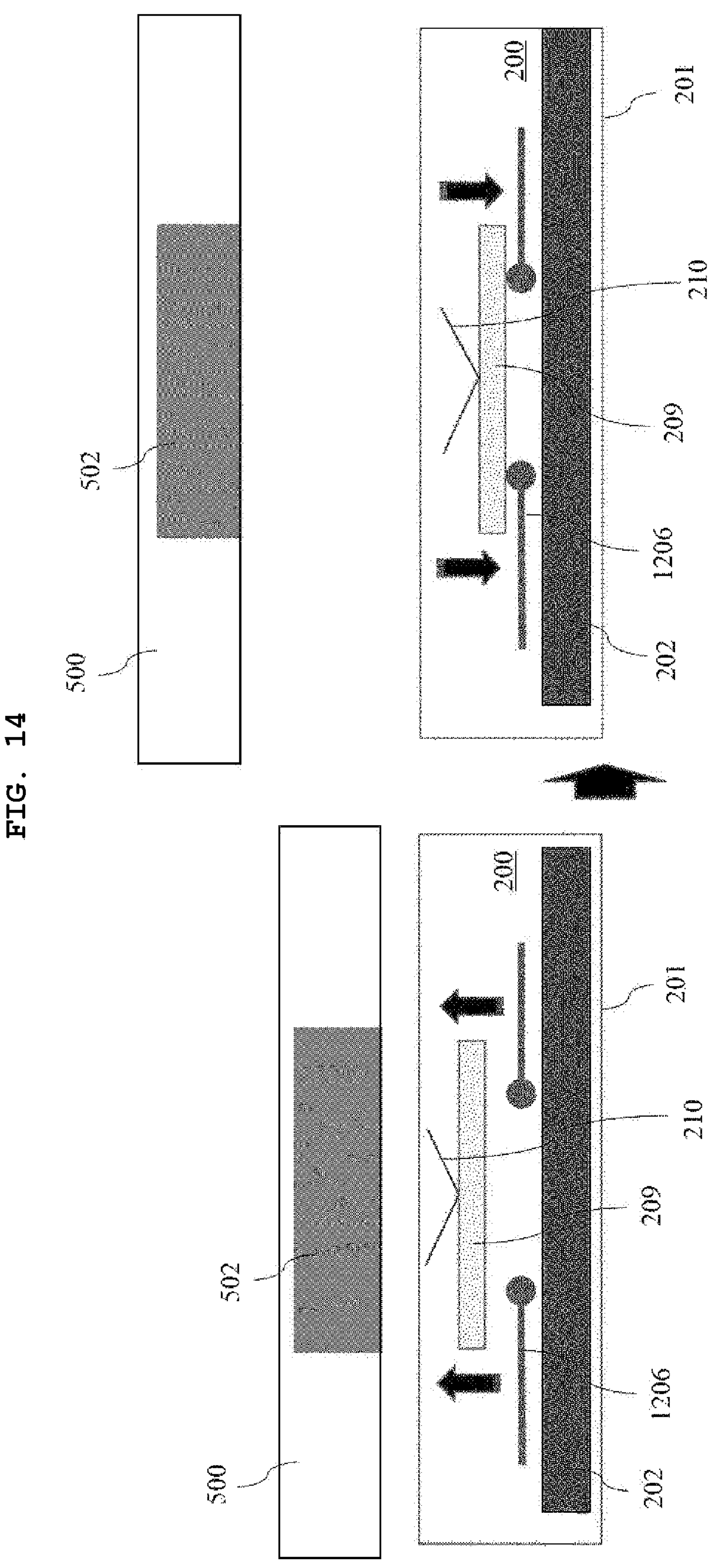

In addition, as another embodiment of a switch, referring to FIG. 11, a switch activator 502 may be provided on a transmitter support 500, and a yoke member 209 made of a metal material may be provided inside a transmitter 200. An elastic member 210 acting an elastic repulsive force toward a power terminal 1206 may be provided on one surface of the yoke member 209. The yoke member 209 may be made of a metal material having conductivity.

In a state in which the transmitter support 500 is coupled to the transmitter 200, due to a magnetic force between the switch activator 502 and the yoke member 209, the yoke member 209 provided inside the transmitter 200 may be moved away from the power terminal 1206 and moved toward the switch activator 502 while compressing the elastic member 210. At this time, the power terminal 1206 may be kept in an off state, so power supply of a battery 204 may be cut off.

On the other hand, when the transmitter support 500 is separated and spaced apart from the housing 201 of the transmitter 200, as the magnetic force of the switch activator 502 is weakened or lost, the yoke member 209 may be moved toward the power terminal 1206. In other words, when the switch activator 502 is moved away from the yoke member 209, due to the elastic repulsive force of the elastic member 210 acting on one surface of the yoke member 209 toward the power terminal 1206, the yoke member 209 may be pushed toward the power terminal 1206 to face the terminal.

When the yoke member 209 faces the power terminal 1206, the power terminal 1206 may be switched from an off state to an on state, and thus power supply of the battery 204 may be started.

A return member 103 corresponding to an actuator 102 may be detachably inserted into the transmitter support 500.

In addition, a protective cap 600 may be detachably coupled to an end of an inserter 100. The protective cap 600 may be detachably coupled to the end of the inserter 100 by screwing or force fitting.

The protective cap 600 may include a blocking member 601 coupled to the inserter 100 and a support member 602 protruding from one surface of the blocking member 601. The support member 602 may support one surface of the housing 201 of the transmitter 200 provided inside the inserter 100 so that the transmitter 200 is kept in a stationary state.

What is claimed is:

1. A continuous analyte meter comprising:

an electrochemical sensor configured to be invasively inserted into the skin;

a transmitter including a main substrate to which a battery is connected and a housing in which the main substrate is accommodated, the housing configured to be attached to the skin and the main substrate controlling a signal measured by the electrochemical sensor;

a needle configured for inserting the electrochemical sensor into the skin; and an inserter provided with an actuator that moves the transmitter and the needle from a first position to a second position so that the needle penetrates the skin or retracts the needle from the second position to a third position, wherein a switch turning on/off power supply of the battery to the main substrate or the electrochemical sensor is provided in the transmitter, and a switch activator interworking with the actuator and turning on the switch to start power supply of the battery is provided, wherein a yoke member is provided in the transmitter, and the yoke member is configured to generate an attractive biasing force that attracts a moving magnet of the switch provided in the transmitter toward the power terminal.

2. The continuous analyte meter of claim 1, wherein the switch is configured to be turned on when contact between the switch activator and the switch is released, a time point at which contact between the switch activator and the switch is released is when the transmitter is moved out of the first position after a first time point at which the transmitter is in the first position, and when the transmitter is in the first position, the switch activator and the switch are configured to be in contact with each other and interfere with each other and the switch is turned off.

3. The continuous analyte meter of claim 1, wherein the switch is configured to be turned on when contact between the switch activator and the switch is released, the second position is a position where movement of the transmitter and the needle is initiated and continues until the transmitter is attached to the skin, and the needle is inserted into the skin, the transmitter and needle are configured to be in the second position at a second time point, a time point at which contact between the switch activator and the switch is released is a third time point at which the needle is moved toward the third position after the second time point, and when the transmitter is in the first position and the second position, the switch activator and the switch are configured to be in contact with each other and interfere with each other and the switch is turned off.

4. The continuous analyte meter of claim 1, wherein the housing is configured to be detachably coupled to a transmitter support, the needle is provided with a needle handle, a return member to which the needle handle is detachably coupled is provided, the actuator comprises the return member, the actuator is configured to move the transmitter support from the first position toward the second position or move the return member from the second position toward the third position, the switch activator is disposed on the return member, and when the return member is configured to be moved toward the third position, contact of the switch activator with the switch is released and the switch is turned on.

5. The continuous analyte meter of claim 1, wherein the housing is detachably coupled to a transmitter support, the needle is provided with a needle handle, a return member to which the needle handle is detachably coupled is provided, the actuator comprises the return member, the transmitter support and the return member are configured to be moved together by the actuator from the first position to the second position, the return member is configured to be separated from the transmitter support, and only the return member is configured to be moved by the actuator from the second position to the third position, and when the return member is separated from the transmitter support, contact of the switch activator with the switch is configured to be released, and the switch is configured to be turned on.

6. The continuous analyte meter of claim 1, wherein the housing is detachably coupled to a transmitter support, the needle is provided with a needle handle, a return member to which the needle handle is detachably coupled is provided, the actuator comprises the return member, the transmitter support and the return member are configured to be moved together by the actuator from the first position to the second position, and before the return member and the transmitter support are separated, the switch activator and the switch are configured to be in contact with each other and interfere with each other and the switch is turned on or off.

7. The continuous analyte meter of claim 1, wherein a protective cap is configured to be detachably coupled to an end of the inserter, and an operation of the actuator is configured to be suppressed before the protective cap is separated from the end of the inserter.

8. The continuous analyte meter of claim 1, wherein the switch activator comprises a magnet provided inside the inserter, and the magnet configured to face the switch and turn on and off the switch.

9. The continuous analyte meter of claim 1, wherein the housing is configured to be detachably coupled to a transmitter support, and the switch activator configured for activating the switch is installed on the transmitter support.

10. The continuous analyte meter of claim 1, wherein the switch activator is a magnet having a magnetic force and is installed inside the inserter, the switch provided in the transmitter comprises:

a power terminal connected to the battery;

a moving magnet facing the power terminal; and a conductive layer formed on one surface of the magnet or disposed between the power terminal and the moving magnet, when the magnet is moved close to the transmitter, the moving magnet is configured to be moved toward the magnet so that the conductive layer is configured to be moved away from the power terminal, and when the magnet is moved away from the transmitter, the moving magnet is configured to be moved toward the power terminal so that the conductive layer configured to switch the power terminal to an on state.

11. The continuous analyte meter of claim 1, wherein an elastic member is provided in the transmitter, and the elastic member is configured to generate an attractive biasing force that attracts the moving magnet of the switch provided in the transmitter toward the power terminal.

12. The continuous analyte meter of claim 1, wherein the switch activator is a magnet having a magnetic force, the switch provided in the transmitter comprises:

a power terminal through which power supply is configured to be turned on/off;

a yoke member configured to be moved relative to the power terminal; and an elastic member configured for supporting the yoke member, when the magnet is moved close to the transmitter, the yoke member is configured to be moved away from the power terminal by the magnetic force between the yoke member and the magnet while compressing the elastic member, and when the magnet is moved away from the transmitter, the yoke member is configured to be moved toward the power terminal by an elastic repulsive force of the elastic member and face the power terminal so that the power terminal is configured to be switched to an on state.

13. A continuous analyte meter comprising:

an electrochemical sensor configured to be invasively inserted into the skin;

a transmitter including a main substrate to which a battery is connected and a housing in which the main substrate is accommodated, the housing configured to be being attached to the skin and the main substrate controlling a signal measured by the electrochemical sensor;

a needle configured to be inserting the electrochemical sensor into the skin; and an inserter provided with an actuator that moves the transmitter and the needle from a first position to a second position so that the needle penetrates the skin or retracts the needle from the second position to a third position, wherein a switch turning on/off power supply of the battery to the main substrate or the electrochemical sensor is provided in the transmitter, and a switch activator interworking with the actuator and turning on the switch to start power supply of the battery is provided, wherein the switch activator is a magnet having a magnetic force, the switch provided in the transmitter comprises:

a power terminal through which power supply is turned on/off;

a moving magnet configured to be moved from the power terminal and having a conductive layer formed on at least one surface thereof; and an elastic member configured for elastically supporting the moving magnet, when the magnet is moved close to the transmitter, the moving magnet is configured to be moved away from the power terminal, and when the magnet is moved away from the transmitter, the moving magnet is configured to be moved toward the power terminal by an elastic repulsive force of the elastic member and face the power terminal so that the power terminal is switched to an on state by the conductive layer.

14. A continuous analyte meter comprising:

an electrochemical sensor configured to be invasively inserted into the skin;

a transmitter including a main substrate to which a battery is connected and a housing in which the main substrate is accommodated, the housing configured to be being attached to the skin and the main substrate controlling a signal measured by the electrochemical sensor;

a needle configured to be inserting the electrochemical sensor into the skin; and an inserter provided with an actuator that moves the transmitter and the needle from a first position to a second position so that the needle penetrates the skin or retracts the needle from the second position to a third position, wherein a switch turning on/off power supply of the battery to the main substrate or the electrochemical sensor is provided in the transmitter, and a switch activator interworking with the actuator and turning on the switch to start power supply of the battery is provided, wherein the switch activator is a magnet having a magnetic force, the switch provided in the transmitter comprises:

a power terminal through which power supply is turned on/off;

a moving magnet configured to be moved from the power terminal and having a conductive layer formed on at least one surface thereof; and an elastic member configured for supporting the moving magnet, when the magnet is moved close to the transmitter, the moving magnet is configured to be pushed apart from the magnet by the magnetic force between the moving magnet and the magnet that have the same polarities and is configured to be moved away from the power terminal while compressing the elastic member, and when the magnet is moved away from the transmitter, the moving magnet is configured to be moved toward the power terminal by an elastic repulsive force of the elastic member and face the power terminal so that the power terminal is switched to an on state by the conductive layer.

* * * * *